(12) United States Patent
Stibrany et al.

(10) Patent No.: US 7,049,457 B2
(45) Date of Patent: May 23, 2006

(54) USE OF AN IONIC HALIDE FREE COPPER CATALYST FOR THE PRODUCTION OF DIALKYL CARBONATES

(75) Inventors: Robert T. Stibrany, Long Valley, NJ (US); Christian P. Mehnert, Clinton, NJ (US); Michael G. Matturro, Lambertville, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 354 days.

(21) Appl. No.: 10/655,995

(22) Filed: Sep. 5, 2003

(65) Prior Publication Data

US 2005/0054868 A1    Mar. 10, 2005

(51) Int. Cl.
C07C 69/96 (2006.01)
(52) U.S. Cl. ...................................... 558/277; 558/260
(58) Field of Classification Search ................ 558/277, 558/260
See application file for complete search history.

(56) References Cited

U.S. PATENT DOCUMENTS

| | | | |
|---|---|---|---|
| 4,318,862 A | 3/1982 | Romano et al. | 260/463 |
| 4,604,242 A | 8/1986 | Dale et al. | |
| 5,391,803 A * | 2/1995 | King et al. | 558/277 |
| 5,498,744 A | 3/1996 | Jentsch et al. | 558/277 |
| 6,010,976 A | 1/2000 | Ryu | 502/156 |
| 6,180,788 B1 | 1/2001 | Stibrany | 544/225 |
| 6,258,923 B1 * | 7/2001 | Tanaka et al. | 528/196 |
| 6,359,163 B1 * | 3/2002 | Mizukami et al. | 558/277 |
| 6,784,277 B1 * | 8/2004 | Boden et al. | 528/196 |
| 2003/0023109 A1 | 1/2003 | Guadalupe et al. | |

FOREIGN PATENT DOCUMENTS

| | | |
|---|---|---|
| EP | 0460732 A1 | 12/1991 |
| EP | 0534545 B1 | 3/1993 |
| WO | WO/0216373 A1 | 2/2002 |

OTHER PUBLICATIONS

"Synthesis of Dimethyl Carbonate from Mehanol, Carbon Monoxide, and Oxygen Catalyzed by Copper Compounds", Romano et al., Ind. Eng. Chem. Prosd. Res. Dev., 1980, 19, p. 396-403.
"A New Type of Support Bipyridine Containing Aromatic Polyamide to CuCl2 for Synthesis of Dimethyl Carbonate (DMC) by Oxidative Carbonylation of Methanol", Sato, Y. et al., J. Mol. Cat. A:Chem, 2000, 151, p. 79-85.
"Applied Homogeneous Catalysis with Organometallic Compounds", Hermmann, W. A., Eds.: VCH, 1996, p. 1750178.

* cited by examiner

Primary Examiner—Golam M. M. Shameem
(74) Attorney, Agent, or Firm—C. L. Bell

(57) ABSTRACT

A non-corrosive process for the preparation of dialkyl carbonate by reacting carbon monoxide, alkanol and an oxygen-containing gas in the presence of a ionic halogen free copper catalyst.

18 Claims, 1 Drawing Sheet

US 7,049,457 B2

USE OF AN IONIC HALIDE FREE COPPER CATALYST FOR THE PRODUCTION OF DIALKYL CARBONATES

BACKGROUND OF THE INVENTION

1. Field of the Invention

The present invention relates to a process for preparing dialkyl carbonates. More particularly, the present invention relates to a process for preparing dialkyl carbonates via the reaction of carbon monoxide, alkanol and an oxygen-containing gas in the presence of an ionic halogen free catalyst. The present invention also relates to a composition useful for the preparation of dialkyl carbonates, the composition comprising an ionic halogen free catalyst, carbon monoxide, an alkanol and an oxygen-containing gas.

2. Description of Related Art

Industrially, dimethyl carbonate (DMC) is used in the production of polycarbonates and has the potential to be used as an environmentally friendly fluid for numerous solvent related applications and conceivably even as a fuel oxygenate (e.g., methyl tertiary butyl ether replacement).

Historically, DMC was prepared from the highly toxic intermediate phosgene, $COCl_2$. Currently, it is prepared via oxidative carbonylation of methanol using an insoluble copper(I) chloride catalyst. This method is based on copper (I) chloride as the catalyst and demonstrated in EP 534,545 B1 and EP 460,732 A1. The overall copper catalyzed reaction of carbon monoxide (CO), methanol ($CH_3OH$) and oxygen ($O_2$) is shown in equation (1) below:

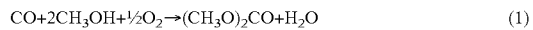
$$CO+2CH_3OH+½O_2 \rightarrow (CH_3O)_2CO+H_2O \qquad (1)$$

The copper(I) chloride catalyst is very insoluble in this system and, thus, is a limiting component in the catalytic cycle. Hydrochloric acid is also added as a component in this oxidative carbonylation system. This was done to prevent the oxidation of Cu(I) to Cu(II) in the presence of oxygen and water since Cu(I) is believed to be the active species in this system. This copper chloride catalyst-based oxidative carbonylation system, which is run between 120 and 160° C., is extremely corrosive and requires costly components (e.g., glass lined reactors). Failure in the glass lining could lead to rupture or explosion. Two other processes for the production of DMC are disclosed in U.S. Pat. Nos. 6,010, 976 and 5,498,744. U.S. Pat. No. 6,010,976 discloses an organotin catalytic reaction of urea with methanol to first form the carbamate, which is further reacted to form DMC, ammonia and carbon dioxide. U.S. Pat. No. 5,498,744 discloses a process that reacts methylnitrite with carbon monoxide over a palladium catalyst to form DMC and $(NO)_x$, which is toxic.

DMC, due to its low toxicity and low atmospheric reactivity, has tremendous growth potential as a possible replacement for methyl tertiary butyl ether (MTBE), as a fluorocarbon solvent replacement in the electronics industry and as an environmentally-friendly solvent for use in the production of polycarbonates. The problems with MTBE, fluorocarbons, and phosgene are widely publicized. The growth of DMC use has been, in part, limited by the difficulties in commercial production. An efficient and environmentally-friendly method for the large-scale production of DMC would be desirable, especially a process that eliminates the need for a chloride-based catalyst which causes corrosion of the reaction vessel and impurities in the resultant product.

There exits a need for a non-corrosive process for the production of dialkyl carbonates, particularly DMC, prepared from carbon monoxide, an oxygen-containing gas and an alcohol. There also exits a need for a soluble catalyst for use in the non-corrosive process for the production of dialkyl carbonates.

SUMMARY OF THE INVENTION

Accordingly, the Applicants have now found an improved non-corrosive process for the production of dialkyl carbonates, and, in particular, DMC, comprising reacting carbon monoxide, an oxygen-containing gas and alcohol in the presence of an ionic halogen free catalyst. The process according to the present invention comprises reacting an ionic halogen free metal catalyst having the formula $LMX_1X_2$ wherein $X_1$ and $X_2$ are independently selected from the group consisting of hydride, triflate, acetate, trifluoroacetate, perfluorotetraphenyl borate, tetrafluoro borate, $C_1$ through $C_{12}$ straight chain or branched alkyl or alkoxy, $C_3$ through $C_{12}$ cycloalkyl or cycloalkoxy, and aryl; wherein M is selected from the group consisting of Cu, Ag, and Au; and wherein L is a nitrogen-containing bidentate ligand with more than 2 nitrogen atoms with carbon monoxide, an alcohol, carbon monoxide and an oxygen-containing gas.

Preferably, the metal catalyst is a copper catalyst, distinguished from commercially used systems by the non-corrosive character (e.g., free of ionic halogens) of the catalysts. Additionally, the ionic halogen free copper catalysts are preferably also soluble in the reaction medium.

In one embodiment according to the present invention, a non-corrosive process for the synthesis of dialkyl carbonate comprises reacting lower alkanols, carbon monoxide, and an oxygen-containing gas in the presence of an ionic halogen free copper catalyst selected from the group consisting of [1,1'(1-butylbenzimidazol-2yl)pentane]copper(II) di(trifluoromethanesulfonate), [1,1'(1-butylbenzimidazol-2yl)pentane]copper(II) di(trifluoroacetate), [2,2'-bis[2-(1-ethylbenzimidazol-2yl)]biphenyl]copper(II) di(trifluoromethanesulfonate), [2,2'-bis[2-(1-ethylbenzimidazol-2yl)]biphenyl]copper(I) (pentafluorobezenesulfonate), [1,1'(1-ethylbenzimidazol-2yl)propane]copper (II) di(pentafluorobenzoate) and mixtures thereof. These catalysts are described in U.S. Pat. No. 6,180,788 B1 and PCT Publication No. WO 02/16373 A1 and are fully incorporated herein by reference. The process of reacting the aforementioned constituents is carried out at a temperature, pressure, and for a time sufficient to form dialkyl carbonate as product.

In another embodiment according to the present invention, a non-corrosive process for the synthesis of dialkyl carbonate comprises reacting lower alkanols, carbon monoxide, and an oxygen-containing gas in the presence of an ionic halogen free copper catalyst comprising at least one of [1,1'(1-butylbenzimidazol-2yl)pentane]copper(II) di(trifluoromethanesulfonate), [1,1'(1-butylbenzimidazol-2yl)pentane]copper(II) di(trifluoroacetate), [2,2'-bis[2-(1-ethylbenzimidazol-2yl)]biphenyl]copper(II) di(trifluoromethanesulfonate), [2,2'-bis[2-( 1-ethylbenzimidazol-2yl)]biphenyl]copper(I) (pentafluorobezenesulfonate), [1,1'(1-ethylbenzimidazol-2yl)propane]copper (II) di(pentafluorobenzoate).

In one embodiment of the present invention, the non-corrosive process entails the preparation of dimethyl carbonate (DMC) by (a) feeding methanol, carbon monoxide and an oxygen-containing gas to a reaction chamber in the presence of an ionic halogen free copper catalyst and (b) taking overhead a dimethyl carbonate-enriched stream and separating substantially pure dimethyl carbonate from said dimethyl carbonate-enriched stream.

DETAILED DESCRIPTION OF THE INVENTION

Figure 1:
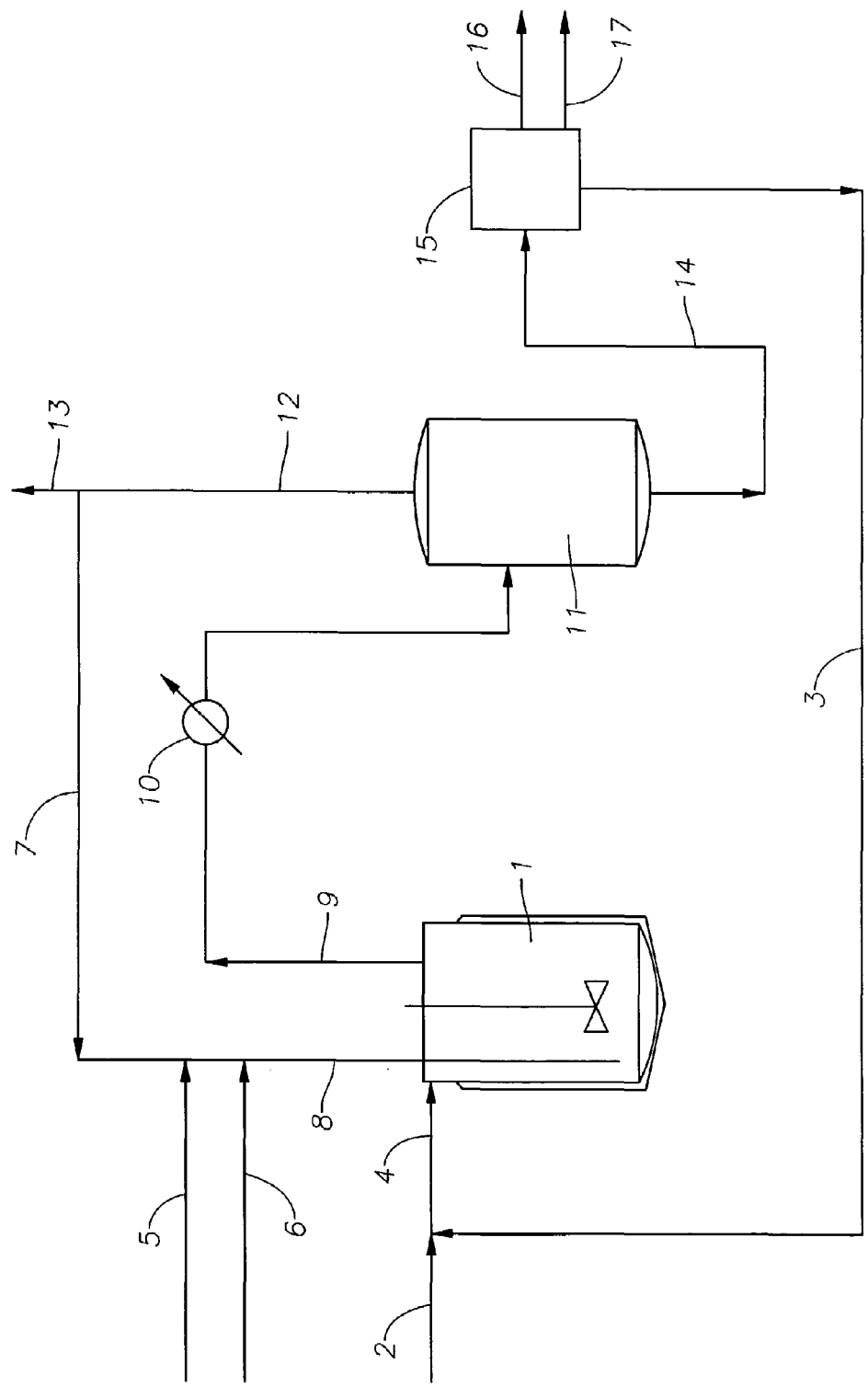
FIG. 1 is a schematic representation of one embodiment of the process according to the present invention.

Accordingly, Applicants have found an unexpected, non-corrosive process for the production of dialkyl carbonates comprising reacting an ionic halogen free catalyst, carbon monoxide, an oxygen containing gas and an alcohol to form the dialkyl carbonate. Applicants have also found an unexpected, non-corrosive composition useful for the production of dialkyl carbonates, wherein the composition comprises an ionic halogen free catalyst, carbon monoxide, an oxygen-containing gas, and an alcohol.

One embodiment according to the process of the present invention comprises reacting a ionic halogen free metal catalyst having the formula $LMX_1X_2$ wherein $X_1$ and $X_2$ are independently selected from the group consisting of hydride, triflate, acetate, trifluoroacetate, perfluorotetraphenyl borate, tetrafluoro borate, $C_1$ through $C_{12}$ straight chain or branched alkyl or alkoxy, $C_3$ through $C_{12}$ cycloalkyl or cycloalkoxy, and aryl; an alcohol, carbon monoxide, and an oxygen-containing gas to form a dialkylcarbonate, wherein M is selected from the group consisting of Cu, Ag, and Au; and L is a nitrogen-containing bidentate ligand with more than 2 nitrogen atoms. In a preferred embodiment, M is copper.

In another embodiment according to the present invention, a non-corrosive process for the synthesis of dialkyl carbonate comprises reacting lower alkanols, carbon monoxide, and an oxygen-containing gas in the presence of an ionic halogen free copper catalyst comprising at least one of [1,1'(1-butylbenzimidazol-2yl)pentane]copper(II) di(trifluoromethanesulfonate), [1,1'(1-butylbenzimidazol-2yl)pentane]copper(II) di(trifluoroacetate), [2,2'-bis[2-(1-ethylbenzimidazol-2yl)]biphenyl]copper(II) di(trifluoromethanesulfonate), [2,2'-bis[2-(1-ethylbenzimidazol-2yl)]biphenyl]copper(I) (pentafluorobezenesulfonate), [1,1'(1-ethylbenzimidazol-2yl)propane]copper(II) di(pentafluorobenzoate).

In one embodiment according to the present invention, a non-corrosive process for the synthesis of dialkyl carbonate comprises reacting lower alkanols, carbon monoxide, and an oxygen-containing gas in the presence of an ionic halogen free copper catalyst selected from the group consisting of [1,1'(1-butylbenzimidazol-2yl)pentane]copper(II) di(trifluoromethanesulfonate), [1,1'(1-butylbenzimidazol-2yl)pentane]copper(II) di(trifluoroacetate), [2,2'-bis[2-(1-ethylbenzimidazol-2yl)]biphenyl]copper(II) di(trifluoromethanesulfonate), [2,2'-bis[2-(1-ethylbenzimidazol-2yl)]biphenyl]copper(I) (pentafluorobezenesulfonate), [1,1'(1-ethylbenzimidazol-2yl)propane]copper(II) di(pentafluorobenzoate) and mixtures thereof.

One embodiment of the process according to the present invention comprises reacting a metal catalyst having the formula $LM X_1X_2$ wherein $X_1$ and $X_2$ are independently selected from the group consisting of hydride, triflate, acetate, trifluoroacetate, perfluorotetraphenyl borate, tetrafluoro borate, $C_1$ through $C_{12}$ straight chain or branched alkyl or alkoxy, $C_3$ through $C_{12}$ cycloalkyl or cycloalkoxy, and aryl, ; an oxygen-containing gas, carbon monoxide, and an alcohol, wherein M is selected from the group consisting of Cu, Ag, and Au; and L is a nitrogen-containing bidentate ligand with more than 2 nitrogen atoms.

A preferred embodiment of this invention is a process using a catalyst having the formula $LM X_1X_2$, wherein L is a nitrogen-containing bidentate ligand represented by the formula:

[AZA'] and [AA'], wherein A and A' are independently selected from the group consisting of

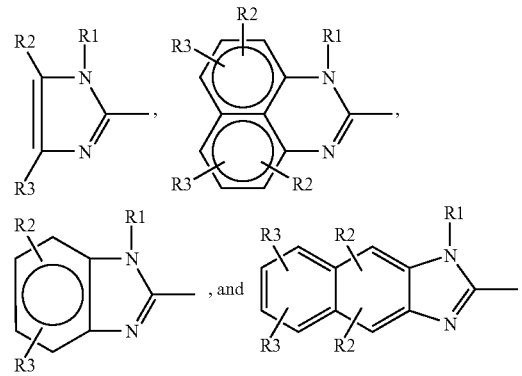

wherein R1 is independently selected from the group consisting of hydrogen, $C_1$ through $C_{12}$ straight chain or branched alkyl, $C_3$ through $C_{12}$ cycloalkyl, aryl, and trifluoroethane;

R2 and R3 are independently selected from the group consisting of hydrogen, $C_1$ through $C_{12}$ straight chain or branched alkyl, $C_3$ through $C_{12}$ cycloalkyl, $C_1$ through $C_{12}$ alkoxy, F, Cl, $SO_3$, $C_1$ through $C_{12}$ perfluoroalkyl, and $N(CH_3)_2$; Z is selected from the group consisting of non-substituted $C_1$, through $C_{12}$ alkyl, $C_3$ through $C_{12}$ cycloalkyl; methoxy; amino; halo; $C_1$, through $C_{12}$ haloalkyl substituted alkyl, cycloalkyl of up to 12 carbon atoms, $C_1$–$C_{40}$ aryl; and $C_1$–$C_{40}$ alkylaryl.

$X_1$ and $X_2$ are independently selected from the group consisting of hydride, triflate, acetate, trifluoroacetate, perfluorotetraphenylborate, tetrafluoroborate, $C_1$, through $C_{12}$ alkyl, $C_1$, through $C_{12}$ alkoxy, $C_3$ through $C_{12}$ cycloalkyl, $C_3$ through $C_{12}$ cycloalkoxy, and aryl.

Accordingly, some of the ligands of the present invention have the following structures:

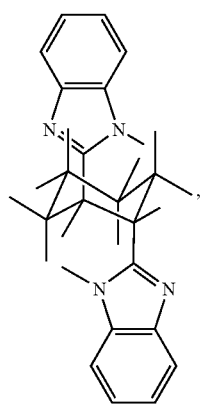

-continued

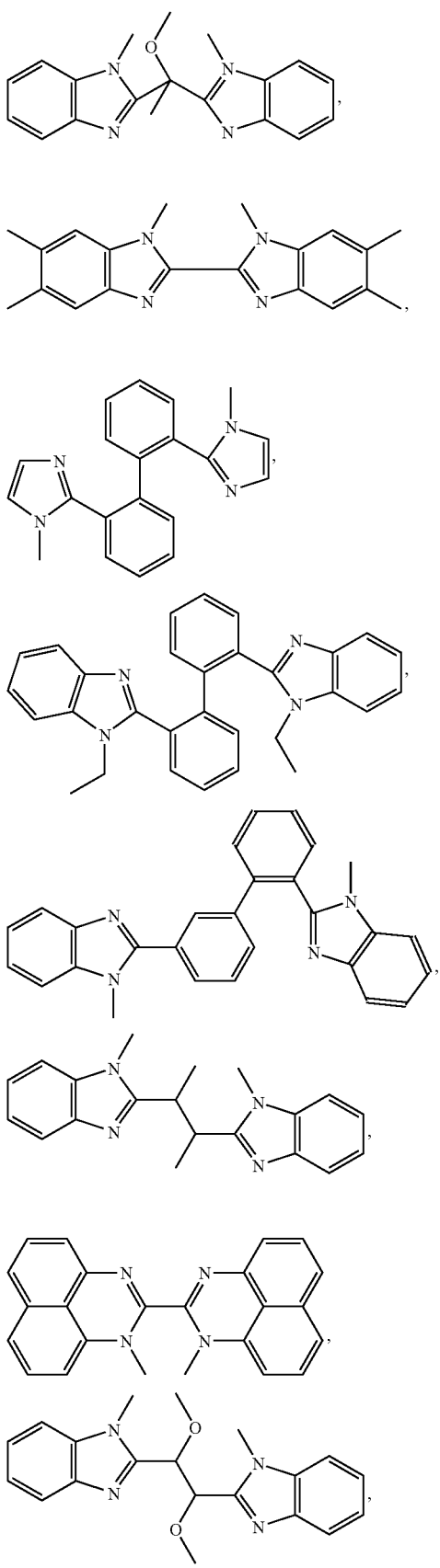

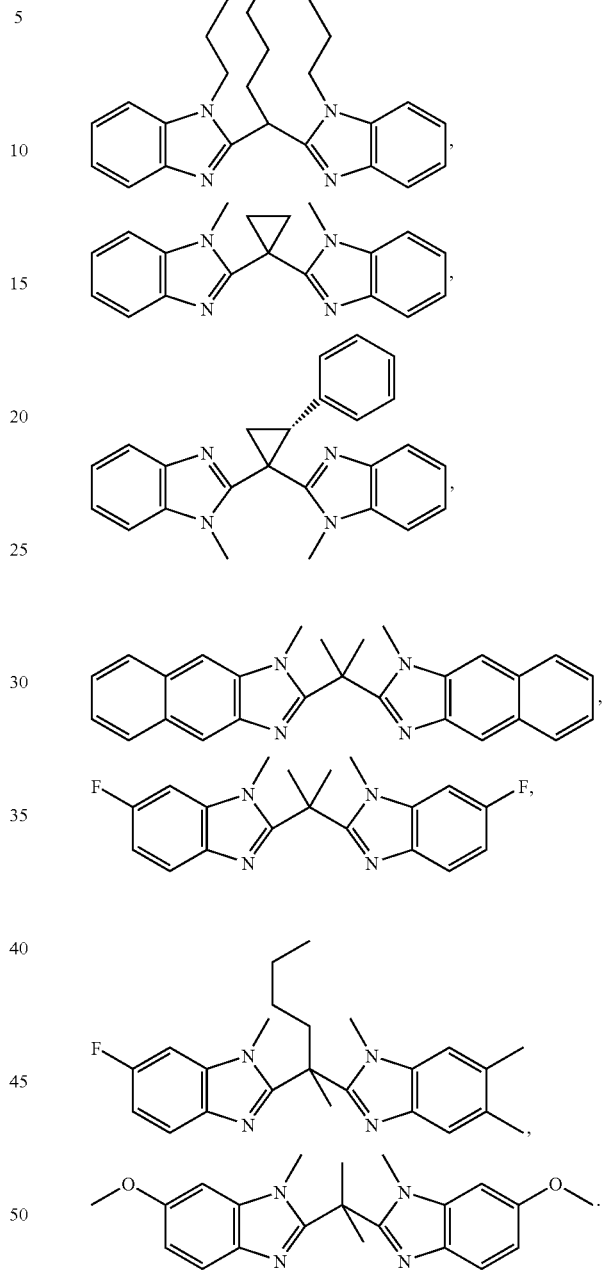

During the synthesis of the dialkyl carbonate, which can be either a continuous or batch process, the molar ratio between carbon monoxide and oxygen is usually higher than that of the stoichiometric value of the reaction and ranges from between about 3:1 to about 100:1, and is preferably from between about 20:1 to about 100:1.

Preferably, the reaction is carried out by dispersing the catalytic system in the reaction medium, basically composed of a mono-alcohol and containig this reaction medium with a gaseous mixture of oxygen and CO.

The gaseous mixture that is put in contact with the alcohol dispersion, can be obtained either by pre-mixing the carbon monoxide and oxygen, or alternatively, by feeding the gases separately and in this latter case contemporaneously or with alternating cycles.

$H_2$, $N_2$, $CO_2$, or $CH_4$ behave as inert gases and do not cause secondary reactions in the reaction system. In particular, it may be convenient, as described in U.S. Pat. No. 4,318,862 (which is incorporated herein by reference), to use carbon monoxide mixed with hydrogen. It is also possible to use gaseous mixtures containing other gases known to those of ordinary skill in the art, for example, helium, argon, ethane and propane.

In one embodiment according to the present invention, the reaction is conveniently carried out at temperatures ranging from about 50° C. to about 200° C., and, preferably from about 1,013 MPa to 10,130 MPa (10 to 100 atmospheres) and with quantities of catalyst ranging from about 10 g/l to about 300 g/l of the reaction medium.

With respect to the recovery of the dialkyl carbonate, conventional separating techniques may be used, such as distillation, filtration, decanting, centrifugation, demixing, absorption on solid absorbents or permeation through selective membranes. These recovery techniques may be used either alone or combined with each other.

The catalytic system and the non-converted reagents, together with any possible variable quantities of dialkyl carbonate and water, may be recycled to the carbonylation reaction.

In one embodiment according to the present invention, the separation of the reaction products is carried out continuously by evaporation resulting from the saturation of the flow of gases fed into the reactor, as set forth in EP-A-0460732, which is incorporated herein by reference. This embodiment of the process has the advantage of avoiding, in a flow process, the movement and recycling of the catalyst to the synthesis reactor.

One embodiment of the process for the continuous preparation of dialkyl carbonate according to the present invention comprises:
  a) feeding an alkanol, carbon monoxide and an oxygen-containing gas into a reaction vessel, kept under reaction conditions, in the presence of soluble copper catalyst, such as, [1,1'(1-butylbenzimidazol-2yl)pentane]copper(II) di(trifluoromethanesulfonate) to form an dialkyl carbonate-enriched stream;
  b) removing the dialkyl carbonate-enriched stream from the reaction vessel; and
  c) separating a substantially pure dialkyl carbonate stream from the dialkyl carbonate-enriched stream;

wherein the composition of the reaction mixture in step (a), is kept substantially constant for a period of time, with a concentration of alkanol equal to or higher than about 30% by weight of the mixture and with a concentration of water equal to or lower than about 10% by weight of the mixture.

The concentration of methanol in the reaction mixture in step (a) may vary from about 30 (weight percent of the total weight of the composition) wt % to about 99 wt % and the concentration of water from about 1 wt % to about 10 wt %. In a preferred method, the reaction mixture in step (a) is composed of ingredients within the following value ranges: methanol from about 40 wt % to about 98 wt %, water from about 2 wt % to about 7 wt %, carbon monoxide from about 7.5 atm to about 75 atm, and oxygen from about 2.5 atm to about 25 atm.

In one embodiment according to the present inventions, the following components are continuously fed to the reaction mixture in step (a): methanol, fresh and recycled carbon monoxide and oxygen-containing gas, the quantity of the fresh reagents being substantially equivalent to that converted to dialkyl carbonate during the reaction of step (a).

One embodiment of the process of the present invention entails the use of a homogeneous soluble ionic halogen free copper catalyst. Another embodiment of the current process involves use of a heterogeneous copper catalyst. It is also contemplated, that the catalyst disposed on a solid support may also be used. Such supports include, but are not limited to, alumina, silica, molecular sieves, and polymers.

The ionic halogen free catalyst, in homogeneous form or insoluble form, may be used in gas phase, liquid phase, fixed bed or fluidized bed reactor systems. The supported catalyst may have a homogeneous form or heterogeneous form of the ionic halogen free catalyst, or mixtures thereof, deposited on the support. The soluble ionic halogen free catalyst may be used on a support in a liquid phase reaction when the dissolution of the soluble catalyst from the support is slow relative to the reaction time. This rate of dissolution may be determined by conventional methods known to those of ordinary skill in the art.

FIG. 1 depicts a suitable system for practicing one embodiment of the process according to the present invention. Reactor 1, equipped with stirring means and heat-exchange jacket (not shown), to which a stream of fresh methanol, and a stream of recycled methanol and dialkyl carbonate are sent via conduits 2 and 3. The feed streams from conduits 2 and 3 are preferably combined and fed to reactor 1 via conduit 4. Carbon monoxide is fed to reactor 1 via conduit 5, and an oxygen-containing gas is fed to reactor 1 via conduit 6. Optionally, a recycle stream containing, inter alia, carbon monoxide is fed to reactor 1 via conduit 7. The reactants from conduits 5, 6 and 7 are combined with one another and are fed to reactor 1 via conduit 8. The overhead stream exiting the reactor via conduit 9 is cooled via heat exchanger 10, the dialkyl carbonate-enriched stream and water are then passed to collector 11 where any residual gases are either recycled via conduit 12 or vented overhead via conduit 13.

The dialkyl carbonate-enriched stream is taken as bottoms via conduit 14 to separator unit 15 in which a stream of substantially pure dialkyl carbonate, i.e., ranging from about 51 wt % to about 100 wt % dialkyl carbonate, is taken via conduit 17 for storage (not shown), water is removed via conduit 16, and residual methanol is recycled to reactor 1 via conduit 3.

The present invention also relates to a composition useful for the preparation of dialkyl carbonates, the composition comprising an ionic halogen free catalyst, carbon monoxide, an alkanol and an oxygen-containing gas, wherein the ionic halogen free catalysts has the formula $LMX_1X_2$ wherein $X_1$ and $X_2$ are independently selected from the group consisting of hydride, triflate, acetate, trifluoroacetate, perfluorotetraphenyl borate, tetrafluoro borate, $C_1$ through $C_{12}$ straight chain or branched alkyl or alkoxy, $C_3$ through $C_{12}$ cycloalkyl or cycloalkoxy, and aryl; an oxygen-containing gas, carbon monoxide, and an alcohol, wherein M is selected from the group consisting of Cu, Ag, and Au; and L is a nitrogen-containing bidentate ligand with more than 2 nitrogen atoms. Preferably, M is Cu. Preferably L and X are as disclosed in paragraphs 17–19. More preferably, the composition useful for the preparation of dialkylcarbonates comprises an ionic halogen free catalyst comprising at least one of [1,1'(1-butylbenzimidazol-2yl)pentane]copper(II) di(trifluoromethanesulfonate), [1,1'(1-butyl-benzimidazol-2yl)pentane]copper(II) di(trifluoroacetate), [2,2'-bis[2-(1-ethylbenzimidazol-2yl)]biphenyl]copper (II) di(trifluoromethanesulfonate), [2,2'-bis[2-(1-ethyl-benzimidazol-2yl)]biphenyl]copper(I) (pentafluorobezenesulfonate), [1,1'(1-ethylbenzimidazol-2yl)propane]copper(II) di(pentafluorobenzoate).

The following non-limiting examples are provided in order to further demonstrate the various embodiments and advantages of the invention. While there have been described what are presently believed to be the preferred embodiments of the invention, those skilled in the art will realize that changes and modifications may be made thereto without departing from the spirit of the invention, and it is intended to claim all such changes and modifications as fall within the true scope of the invention.

EXAMPLE 1

1,1'bis(1-hydrobenzimidazol-2yl)methane, HBBIM

In a 1 L round bottom flask equipped with a Dean Stark trap, 24.06 g (0.23 mol) of malonic acid, 50.00 g of (0.46 mol) 1,2-phenylenediamine, and 85 g of polyphosphoric acid were added sequentially. The mixture was heated at 210° C. for 3.5 hours with stirring. The mixture was cooled to 150° C. and then poured into 1 L of water. A blender was used to grind the slurry. The mixture was then neutralized to pH 8 with ammonium hydroxide. The solid was collected by filtration and repeatedly washed with water. The solid was dried to constant weight under vacuum at 80° C. for 24 h. $C_{15}H_{12}N_4$, FW=248.29. Yield: 33.1 g, 58%; mp 331° C. (dec.); $^1$H NMR ($CD_3SO_2CD_3$): δ=7.53(q, J=3.1 Hz, 4H), 7.16(q, J=3.1 Hz, 4H), 4.54(s, 2H), 2.51(s, 2H); $^{13}$C NMR ($CD_3SO_2CD_3$) δ 150.6, 139.1, 121.9, 115.1, 29.7.—$R_f$=0.28 (Etoac), FD MS 248.2. IR (KBr pellet, cm$^{-1}$) 1622, 1590, 1544, 1530, 1487, 1435 s, 1309, 1271 s, 1031 s, 999, 738 s, 618, 466. Anal. Calcd for N, 22.57; H, 4.87; C, 72.56. Found: N, 22.57; H, 4.86; C, 72.36.

EXAMPLE 2

1,1'bis(1-butylbenzimidazol-2yl)pentane, tributBBIM

A 23.00 g (0.093 mol) quantity of HBBIM was placed in a 300 mL round bottom flask with a side arm and a bubbler. This was followed by the addition of 25 mL of DMSO. Under a flow of nitrogen 6.0 g of sodium hydride (60% dispersion in mineral oil) was added over one hour with stirring. Then 25.00 mL (0.220 mol) of 1-iodobutane was added dropwise over one hour. The reaction mixture was left stirring under nitrogen for 48 hours. The reaction mixture was quenched with water and then an additional 400 mL of water was added. After the quenched reaction mixture was stirred for one half hour, a biphasic solution was obtained. The organic layer was extracted with cyclohexane and was washed with water. The volatiles were removed under reduced pressure to leave a dark oil, which was chromatographed on silica gel using methylene chloride as the eluent. The solvent was removed under reduced pressure to give a very pale-pink oil which crystallized upon standing. $C_{27}H_{36}N_4$, FW=416.61. Yield: 20.44 g, 67%. mp 82–83° C.—$^1$H NMR ($CDCl_3$): δ=7.79(m, 2H), 7.24(m, 6H), 4.88(t, J=7.9 Hz, 1H), 4.16(d sp, J=5.0 Hz, J=40.9 Hz, 4H), 2.59(m, 2H), 1.44(m, 4H), 1.16(m, 4H), 1.10(m, 2H), 0.99(m, 2H), 0.89(t, J=6.8 Hz, 3H), 0.61(t, J=7.0 Hz, 6H). $^3$C NMR ($CDCl_3$): δ=151.8, 142.4, 135.6, 122.6, 122.0, 119.6, 109.7, 44.0, 40.9, 31.5, 31.2, 30.1, 22.5, 20.0, 14.0, 13.4.—$R_f$=0.73 (Etoac)—FD MS 416.1, IR (KBr pellet, cm$^{-1}$) 3050 m, 2955 m, 2931 m, 2862 m, 1613 w, 1501 m, 1458 s, 1400 s, 1331 m, 1285 m, 1008 m, 933 m, 743 s, 434 w.

EXAMPLE 3

[1,1'(1-butylbenzimidazol-2yl)pentane]copper(II) dibromide—abbreviated "Cu(tributBBIM)Br$_2$"

[1,1'bis(1-butylbenzimidazol-2yl)pentane]copper(II) dibromide, Cu(tributBBIM)Br$_2$ In an argon glove box, a 10.62 g (0.0475 mol) quantity of copper (II) dibromide was dissolved in 900 mL of absolute ethanol followed by the addition of 180 mL of triethyl orthoformate (TEOF). Then 18.00 g (0.0432 mol) of tributBBIM was added to the solution. The solution was heated at reflux for a half-hour. Upon cooling the solution, a maroon precipitate was collected by filtration and washed with TEOF followed by pentane. The solid was dried under high vacuum. $C_{27}H_{36}Br_2CuN_4$, FW=639.96. Yield: 17.47 g, 63%. mp (stage) 221° C. (KBr pellet, cm$^{-1}$) 3097 w, 3061 w, 3030 w, 2957 s, 2930 s, 2872 m, 2858 m, 1613 w, 1510 s, 1454 s, 755 s, 505 w. Anal. Calcd for N, 8.75; H, 5.67; C, 50.67; Cu, 9.94; Br, 24.97. Found: N, 8.65; H, 5.59; C, 50.11; Cu, 10.00; Br, 25.60.

EXAMPLE 4

[1,1'(1-butylbenzimidazol-2yl)pentane]copper(II) di(trifluoroacetate)—abbreviated "Cu(tributBBIM)(TFA)$_2$"

A 271 mg (0.42 mmol) quantity of Cu(tributBBIM)Br$_2$ was placed in a 125 mL Erlenmeyer flask containing 40 mL of methylene chloride to give a maroon solution. Then 188 mg (0.85 mmol) of silver trifluoroacetate was added to the solution and the mixture was allowed to stir. After about an hour, the mixture had become blue with some suspended gray solid. The mixture was stirred overnight and filtered through a 0.20% Teflon® membrane to give a brilliant clear blue solution. The solvent was removed under a stream of nitrogen to give a blue-purple glass. This solid was placed in a vacuum oven at 60° C. to remove any remaining solvent.

EXAMPLE 5

Cu(tributBBIM)(TFA)$_2$ Catalyzed Production of Dimethyl Carbonate (DMC)

In an Ar glovebox, 21.1 mg (0.028 mmol) of Cu(tributBBIM)(TFA)$_2$ was placed in a vial containing 2.5 mL of $CD_3OH$ to give a blue-green solution, which was transferred into a high-pressure sapphire NMR tube with a volume of 6.0 mL. The tube was sealed and taken from the glovebox. The sample was first charged with nitrogen to 200 psig and then with oxygen to 250 psig. This was followed by pressurization with $^{13}CO$ to 500 psig. The NMR of the reaction mixture was measured immediately thereafter. The tube was then placed in a shaker at 80° C. overnight. After the NMR tube and contents were cooled to ambient temperature, the NMR of the sample was measured again. The solution was still blue-green with no visible decomposition. $^{13}$C-NMR δ 158 (C~O, DMC), δ 126 (CO$_2$). GC 2.4 area %), (MS=m/z 97.1 ($CD_3O(^{13}CO)OCD_3$) cald.=97.02); semi-quantitative turnover based on GC; 1.50 mmol DMC/0.030 mmol Cu=50 turnovers per Cu atom.

EXAMPLE 6

DMC Production is Conducted Via a Batch Process

A 19.2 mg quantity of [1,1'(1-butylbenzimidazol-2yl) pentane]copper(II) di(trifluoromethanesulfonate) was dissolved in 25 mL of reagent grade methanol. The solution was placed in a 50 cm$^3$ autoclave. The autoclave was charged to 690 kPa with oxygen and was then pressurized to 6890 kPa with carbon monoxide. The autoclave was heated to 80° C. and the pressure was maintained at 10330 kPa with carbon monoxide for 3 hours. The reaction mixture was cooled to ambient temperature and analysis by GC showed the sample contained 1.4 wt. % dimethylcarbonate.

EXAMPLE 7

DMC Production is Conducted Via a Continuous Process

In a 150 cm$^3$ continuous flow through reactor containing [1,1'(1-butylbenzimidazol-2yl)pentane]copper(II) di(trifluoromethanesulfonate) at a concentration of 0.04 mol/L in 60 mL methanol, the reaction was run at 100° C. at a pressure of 2480 kPa at a flow rate of 15 mL/min. air and 40 mL/min. carbon monoxide. Dimethylcarbonate was generated at a constant rate of 0.02 mol/hr. for 40 hrs.

We claim:

1. A process for the preparation of dialkyl carbonate comprising:
   reacting carbon monoxide, at least one alkanol and an oxygen-containing gas in the presence of a ionic halogen free copper catalyst, thereby forming said dialkyl carbonate in a crude dialkyl carbonate product.

2. The process of claim 1, wherein said catalyst is selected from the group consisting of: [1,1'(1-butylbenzimidazol-2yl)pentane]copper(II) di(trifluoromethanesulfonate), [1,1'bis(1-ethylbenzimidazol-2yl)propane]copper(II) di(tosylate), rac-[2,2'-bis[2-(1-ethylbenzimidazol-2yl)]biphenyl]copper(II) di(trifluoroacetate), rac-[[S-2,2'-bis[2-(1-butylimidazol-2yl)]biphenyl]copper(II) di(pentafluorobenzoate, and rac-[[S-2,2'-bis[2-(1-octylbenzimidazol-2yl)]biphenyl]copper(II) di(pentafluorophenylsulfonate).

3. The process of claim 1, wherein the molar ratio of said carbon monoxide to said oxygen-containing gas is between about 3:1 to about 100:1.

4. The process of claim 1, wherein said reaction step is carried out at a temperature between about 40° C. to about 200° C. and at a pressure between about atmospheric pressure up to about 1400 Mpa.

5. The process of claim 1, wherein said catalyst is present from about 10 g/l to 300 g/l of the total reaction mixture.

6. The process of claim 1, further comprising recovering a dialkyl carbonate enriched stream from said crude dialkyl carbonate product.

7. The process of claim 6, wherein said recovery step is at least one step selected from the group consisting of distillation, filtration, decanting, centrifugation, demixing, absorption on solid absorbents and permeation through selective membranes.

8. The process of claim 1, wherein said alkanol is methanol and said dialkyl carbonate is dimethyl carbonate.

9. The process of claim 8, wherein said alkanol is present in a concentration from about 30 wt % to about 95 wt % of the total reaction mixture.

10. The process of claim 8, further comprising water in a concentration from about 1 wt % to about 10 wt % of the total reaction mixture.

11. The process of claim 8, further comprising an inert gas.

12. The process of claim 1, wherein said catalyst is a homogeneous catalyst.

13. The process of claim 1, wherein said catalyst is a heterogeneous catalyst.

14. The process of claim 1, wherein said catalyst comprises a support.

15. The process of claim 1, wherein said support comprises at least one material selected from the group consisting of alumina, silica, and a polymeric material.

16. The process of claim 1, wherein said process is a continuous process.

17. The process of claim 1, wherein said process is a batch process.

18. The process of claim 11 wherein said inert gas is selected from the group comprising an inert gas.

* * * * *